United States Patent
Ollivier

(10) Patent No.: US 10,182,730 B2
(45) Date of Patent: *Jan. 22, 2019

(54) LEAD FOR AN ACTIVE IMPLANTABLE MEDICAL DEVICE WITH A CHIP FOR ELECTRODE MULTIPLEXING

(71) Applicant: SORIN CRM SAS, Clamart (FR)

(72) Inventor: Jean-François Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 631 days.

This patent is subject to a terminal disclaimer.

(21) Appl. No.: 14/696,064

(22) Filed: Apr. 24, 2015

(65) Prior Publication Data
US 2015/0223713 A1 Aug. 13, 2015

Related U.S. Application Data

(63) Continuation of application No. 13/325,930, filed on Dec. 14, 2011, now Pat. No. 9,020,574.

(30) Foreign Application Priority Data

Dec. 14, 2010 (FR) ..................... 10 60452

(51) Int. Cl.
*A61N 1/05* (2006.01)
*A61B 5/042* (2006.01)
(Continued)

(52) U.S. Cl.
CPC .......... *A61B 5/0408* (2013.01); *A61B 5/0215* (2013.01); *A61B 5/686* (2013.01);
(Continued)

(58) Field of Classification Search
CPC ..... A61B 5/0408; A61B 5/0215; A61B 5/686; A61B 2562/125; A61N 1/05; A61N 1/0587; H01R 43/20
See application file for complete search history.

(56) References Cited

U.S. PATENT DOCUMENTS

| 4,628,934 A | 12/1986 | Pohndorf et al. |
| 5,535,752 A | 7/1996 | Halperin et al. |

(Continued)

FOREIGN PATENT DOCUMENTS

| EP | 1 036 572 | 9/2000 |
| EP | 1 938 861 | 7/2008 |

(Continued)

OTHER PUBLICATIONS

Foreign Search Report on French Application No. 1060452, dated Aug. 4, 2011, 2 pages.

(Continued)

*Primary Examiner* — Lee S Cohen
*Assistant Examiner* — Erin M Cardinal
(74) *Attorney, Agent, or Firm* — Foley & Lardner LLP

(57) ABSTRACT

A lead for active implantable medical devices comprising a chip, notably for electrode multiplexing. The lead includes an insulating supporting tube interposed in a flexible elongated tube, with a central bore coaxial with the lumen of the lead. The supporting tube comprises on its surface at least one crossing conductive strip extending in the axial direction. A chip on a flexible substrate is disposed with a bent or curved conformation in a receptacle of the supporting tube isolated from the conductive strip. An electrode, e.g., for cardiac sensing/pacing, carried by the supporting tube is electrically connected to an outer conductive pad of the chip. The conductive strip is connected (i) at each end, face to face to a conductive connection, housed in the sheath, and (ii) in a central region, to an inner conductive pad of the chip.

20 Claims, 4 Drawing Sheets

(51) Int. Cl.
  *A61B 5/0408* (2006.01)
  *A61B 5/0215* (2006.01)
  *A61B 5/00* (2006.01)
  *H01R 43/20* (2006.01)

(52) U.S. Cl.
  CPC ............ *A61N 1/05* (2013.01); *A61N 1/0587* (2013.01); *H01R 43/20* (2013.01); *A61B 2562/125* (2013.01); *Y10S 439/909* (2013.01); *Y10T 29/49171* (2015.01)

(56) References Cited

U.S. PATENT DOCUMENTS

| | | | |
|---|---|---|---|
| 6,117,088 | A | 9/2000 | Kreizman et al. |
| 6,248,080 | B1 * | 6/2001 | Miesel ................. A61B 5/0215 600/311 |
| 6,418,348 | B1 * | 7/2002 | Witte ..................... A61N 1/056 607/119 |
| 6,463,333 | B1 | 10/2002 | Ollivier |
| 6,473,653 | B1 * | 10/2002 | Schallhorn ............... A61N 1/05 600/393 |
| 7,974,705 | B2 | 7/2011 | Zdeblick et al. |
| 9,020,574 | B2 * | 4/2015 | Ollivier ............... A61B 5/0215 439/909 |
| 2002/0156417 | A1 * | 10/2002 | Rich .................... A61B 5/0031 604/65 |
| 2002/0161422 | A1 | 10/2002 | Swanson et al. |
| 2005/0070982 | A1 | 3/2005 | Heruth et al. |
| 2005/0148832 | A1 | 7/2005 | Reghabi et al. |
| 2008/0077186 | A1 | 3/2008 | Thompson et al. |
| 2008/0114230 | A1 | 5/2008 | Addis |
| 2008/0177343 | A1 | 7/2008 | Dal Molin et al. |
| 2008/0255647 | A1 * | 10/2008 | Jensen .................... A61N 1/05 607/119 |
| 2009/0192572 | A1 | 7/2009 | Dal Molin et al. |
| 2009/0292242 | A1 | 11/2009 | Konishi |
| 2011/0024186 | A1 | 2/2011 | Receveur et al. |

FOREIGN PATENT DOCUMENTS

| | | |
|---|---|---|
| EP | 2 082 684 | 7/2009 |
| WO | WO-2006/069322 | 6/2006 |
| WO | WO-2010/091435 | 8/2010 |

OTHER PUBLICATIONS

Zimmerman et al., "A Seamless Ultra-Thin Chip Fabrication and Assembly Process," Electron Devices Meeting IEDM '06, Dec. 11-13, 2006, 3 pages.

* cited by examiner

LEAD FOR AN ACTIVE IMPLANTABLE MEDICAL DEVICE WITH A CHIP FOR ELECTRODE MULTIPLEXING

CROSS-REFERENCE TO RELATED PATENT APPLICATIONS

This application is a continuation of U.S. application Ser. No. 13/325,930, filed Dec. 14, 2011, now U.S. Pat. No. 9,020,574, which claims the benefit of and priority to French Application No. 1060452, filed Dec. 14, 2010, both of which are hereby incorporated by reference herein in their entireties.

BACKGROUND

The present invention relates to "medical devices" as defined by the 14 Jun. 1993 Directive 93/42/CE of the Council of the European Communities, and more particularly to "active implantable medical devices" as defined by the 20 Jun. 1990 Directive 90/385/EEC of the Council of the European Communities, including those devices that continuously monitor a patient's heart rhythm and deliver to the heart, if necessary, electrical pulses for stimulation, resynchronization, cardioversion and/or of defibrillation, as well as neurological devices, drug delivery systems, cochlear implants, implantable biological sensors, and similar devices, and as well as devices for measuring pH or intracorporeal impedance (such as the trans-pulmonary impedance or the intracardiac impedance).

For the collection or detection (the terms being used interchangeably herein) of signals, and for the delivery of pulses for stimulation, such as for cardiac pacing, active implantable medical devices use electrodes that are incorporated into a lead that is connected to the generator of the device. The generator contains the signal collection circuits and the pulse generator circuits. The electrodes are intended to come into contact with the tissues from which an electrical signal is to be collected, and the tissues to be stimulated, such as the myocardium, nerve, or muscle tissues, as the case may be. In the case of a device for cardiac diagnosis and therapy, these electrodes can be endocardial (placed in a cavity of the myocardium in contact with the wall of the myocardium), epicardial (placed on an outside wall of the myocardium, in particular to define a reference potential, or to apply a shock) or intravascular (implanted, for example, in the coronary sinus artery to a location opposing the wall of the left ventricle).

A first aspect of the development of these active implantable devices is the increasing number of electrodes, particularly for those devices called "multisite" devices, that allow for choosing between different stimulation/detection sites and optimizing the operation of the device. The increasing number of electrodes can also result from the presence at a same level of the lead of several sector electrodes (which are electrodes specifically directed in a radial direction with respect to the lead, at the stimulation site), with the option to select one or another of these sector electrodes to optimize the delivery of pulses to the selected site. This is particularly true for leads implanted in the coronary venous system, for indirect stimulation of a left cavity: with several sector electrodes, it is relatively easy to choose the one that faces the wall of the epicardium in front of the cavity and in contact with the wall and thus to avoid phrenic nerve stimulation.

Another aspect of the development of implantable devices is the integration of different sensors into the lead, especially blood pressure or acceleration sensors, including endocardial acceleration (EA) sensors. The signals collected by these sensors provide information representative of the instantaneous hemodynamic status of the patient, allowing for more effective control of the various functions of the device.

These lead sensors also require a specific connection for the transmission of signals from the sensor, typically located at the distal end of the lead, to the generator connected at the opposite, proximal end. This connection is specific to the sensor and is superimposed on the specific connections existing between the generator and the various electrodes located in the distal region of the lead.

In any case, to accommodate as many conductors as there are electrodes would lead to both unacceptable dimensions for the lead and difficulties in manufacturing the lead, especially at the connecting link between the lead at its proximal end and the implantable generator to which it is coupled.

These developments, therefore, require the introduction of multiplexing electronic circuits to manage the exchange of multiple signals between the lead (electrodes and/or sensors) and the generator, and vice versa. Multiplexing is provided in situ, close to the electrodes by an electronic circuit (hereinafter simply called "chip") embedded in the distal part of the lead, at or in the vicinity of its end (wherein the signals are collected and/or the pulses are to be delivered).

The EP 1938861 A1 (US counterpart: US2008/0177343) and EP 2082684 A1 (US counterpart: US2009/0192572) (all commonly owned by Sorin CRM S.A.S, previously known as ELA Medical, of Clamart France) describe such a lead having a plurality of electrodes, for example, ten electrodes, near its distal end associated with a chip, hermetically encapsulated in the vicinity of the electrodes in a rigid ring, providing the multiplexing/demultiplexing of the electrodes with a common bus formed by two insulated conductors extending along the entire length of the lead to the proximal connector, allowing the coupling with the generator, the latter being equipped with a counterpart demultiplexing/multiplexing circuit.

WO2010/091435 A2 and WO 2006/069322 A2 (Proteus Biomedical, Inc.) describe a system in which a common two-wire bus transmits signals from/to sector-addressable electrodes formed on "satellites" located on the lead at regular intervals. A multiplexing/demultiplexing chip is mounted inside the lead, and connected to the wires of the bus by means of welded micro-springs. The construction described, however, only leaves the lead with an internal lumen having a very small internal diameter relative to its outside diameter, due to the size of the chip and connections to the wires. This constraint limits the application of this technique to electrodes located at the distal end of lead, because the small lumen diameter would not allow the use of traditional techniques of implantation, unless by greatly increasing the outer diameter of the lead at the location of the those distal electrodes, which would in turn limit the applications. In addition, the implementation technology is extremely difficult to implement and its reliability over time has not been proven.

SUMMARY

It is, therefore, an object of the present invention to provide a lead having an internal lumen with a diameter comparable to that of the currently existing leads (typically having an inner diameter of 0.55 mm or 1.65 French), and electrical insulation over conductors and the chip.

It is another object of the present invention to provide a such lead with an outer diameter comparable to currently existing leads (typically an external diameter of 1.6 mm or 4.8 French or even 4 French), with a relatively constant diameter along the length of the lead, namely a lead configuration known as "monodiameter."

It is a further object of the present invention to provide such a lead with a chip natively encapsulated thanks to the geometry and configuration of the elements of the lead, with excellent electrical insulation and mechanical protection against both torsional stress and bending.

The present invention is directed to a lead of the above known type, for example as disclosed in the WO 2010/091435 A2 cited above, comprising: an elongated flexible sheath with a central lumen; at least one conductive connection housed in the lumen of the sheath; a rigid cylindrical supporting tube in an isolating material, with a crossing central bore, the supporting tube being interposed in the sheath, namely, being inserted in the sheath so that its crossing bore is coaxial (i.e., in axial alignment) with the lumen of the sheath, the supporting tube including in its surface a cavity forming a receptacle for a chip, opening into a central region of the supporting tube; at least one electrode provided on the sheath surface; and at least one electronic circuit on a substrate comprising a chip, and at least two conductive pads respectively connected to the conductive connection and to the electrode, the chip having an outer conductive pad on one side of the substrate and on the opposite side an inner conductive pad, the electrode being electrically connected to the outer conductive pad of the chip; and a feedthrough conductor connected in a central region to the inner conductive pad of the chip.

Preferably, the substrate of the chip is a flexible substrate, disposed with a curved conformation in the receptacle of the supporting tube. In one embodiment, the conductive connection housed by the sheath includes a disconnect at the supporting tube location, and the feedthrough conductor is a conductive strip formed at the surface of the supporting tube, extending in the axial direction throughout the supporting tube, and connected at both ends face-to-face with the conductive connection housed in the sheath. Preferably, the electrode is for signal collection and/or pulse delivery, and more particularly is for cardiac sensing/pacing.

In another embodiment, the chip has a flexible substrate with an outer conductive area on one side of the substrate and an inner conductive pad on the opposite side, and is disposed with a bent conformation in the receptacle of the supporting tube. Preferably, a sensing/pacing electrode is carried by the supporting tube and is electrically connected to the exterior conductive pad of the chip. As for the conductive strip, it is preferably connected (i) at each end face to face to the conductive connection(s) housed in the sheath, and (ii) in a central region, to the inner conductive area of the chip.

In one embodiment, the insulating material of the supporting tube is a ceramic. Preferably, the lead has a unique ring electrode the shape of which is a conductive sleeve circumferentially extending around the entire periphery of the supporting tube and slipped over the central region of the supporting tube.

In one embodiment, the lead has a plurality of sector electrodes isolated from each other, circumferentially distributed around the perimeter of the supporting tube and each connected to a corresponding plurality of conductive pads outside of the chip.

Preferably, the overall diameter of the lead is essentially constant in the region of the supporting tube and of the electrode, and equal to the diameter of the flexible sheath.

In a preferred embodiment, the lead has two separate conductive connections housed in the lumen of the sheath, the supporting tube including two corresponding crossing separate conductive strips that are isolated from each other and more preferably formed in diametrically opposed regions on the surface of the supporting tube.

Advantageously, the present invention results in a lead offering the practitioner a conventional lead configuration, allowing for its implantation using, and without changing, the normal implantation techniques. Also advantageously, the present invention provides a lead that can be manufactured by implementation of standard processes in the manufacture of leads, that is to say proven processes that can be implemented at lower cost.

BRIEF DESCRIPTION OF THE DRAWINGS

Further features, characteristics, and advantages of the present invention will become apparent to a person of ordinary skill in the art from the following detailed description of embodiments of the present invention, made with reference to the annexed drawings, in which like reference characters refer to like elements, and in which:

FIGS. 9 to 11 show the successive steps for manufacturing the section of a second embodiment of the lead including the chip and several sector electrodes, in which FIG. 9 illustrates a supporting tube for supporting a sector electrode, FIG. 10 illustrates the supporting tube of FIG. 9 after installation of an insulating sleeve, and FIG. 11 illustrates the supporting tube of FIG. 10 after installation of the sector electrodes.

DETAILED DESCRIPTION

With reference to the drawings, preferred embodiments of the present invention will now be described.

Figure 6:
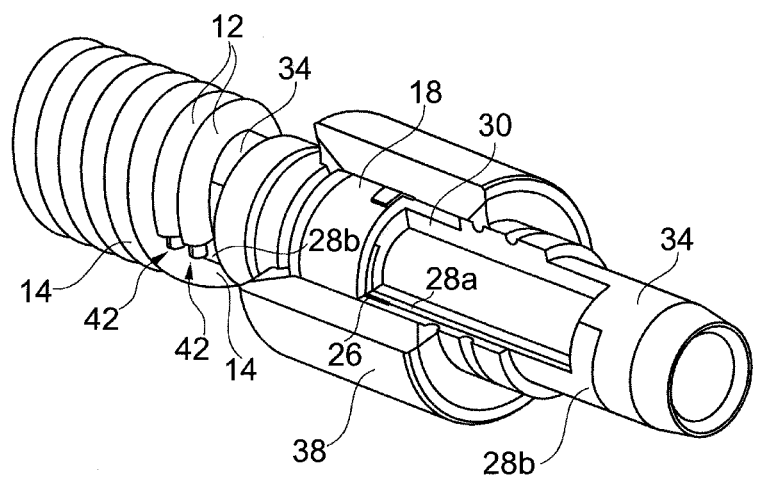
Figure 7:
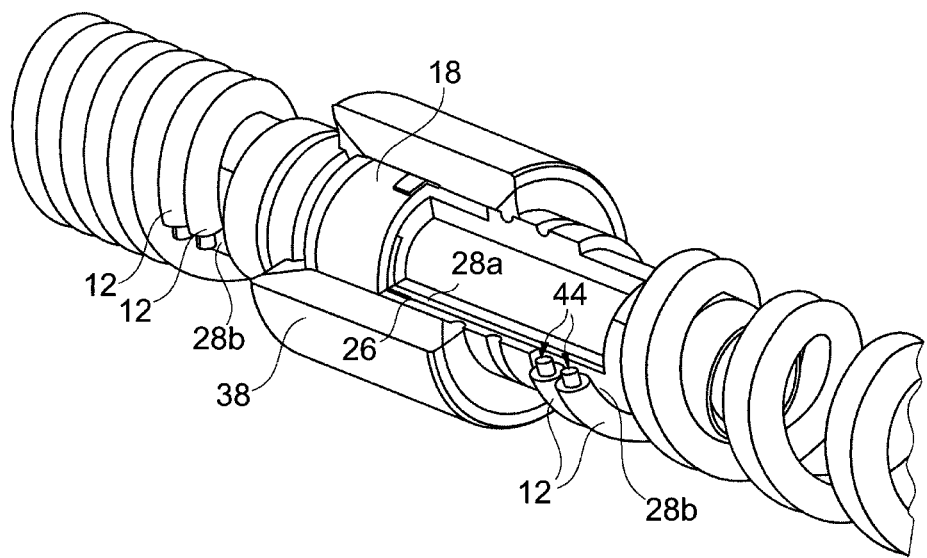
Figure 8:
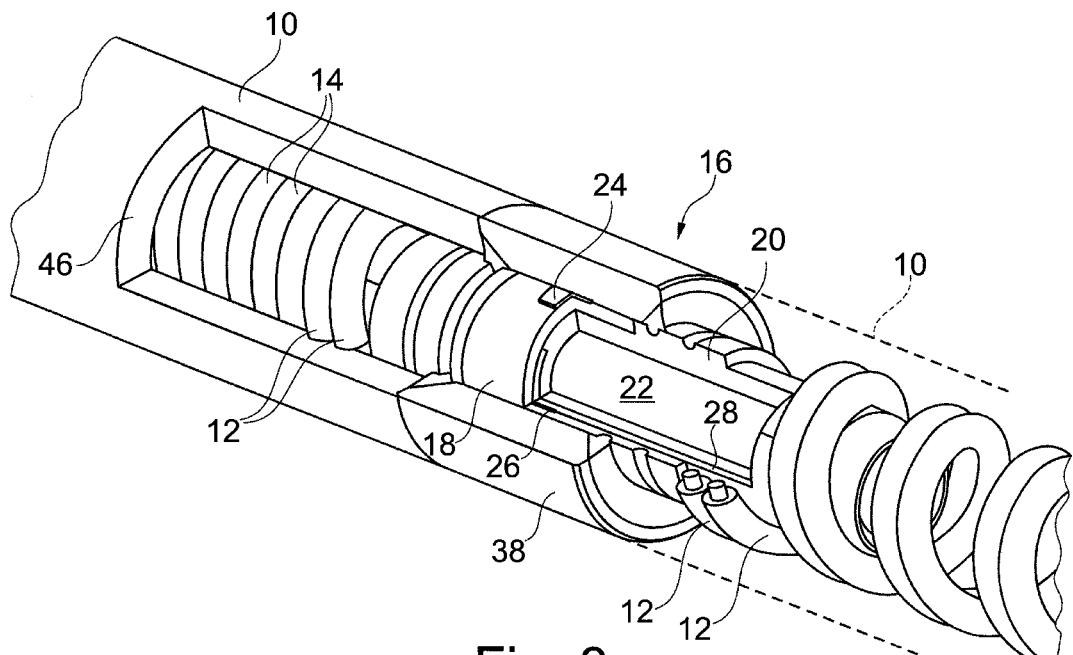

With reference to FIG. 8, a portion of a lead in accordance with a first embodiment of the present invention is illustrated with its various components, as obtained after execution of the various manufacturing steps illustrated in FIGS. 1 to 7. Reference 10 generally designates the body of a known lead used for cardiac detection/stimulation, for which only a portion is shown (FIGS. 1-8), which portion is generally located near the distal end, including am electrode, e.g., a detection and/or stimulation electrode. The electrode is illustrated as an annular electrode in the first embodiment shown in FIGS. 1-8. The electrode is illustrated as a plurality of sector electrodes in the second embodiment shown FIGS. 9-11 (described further below).

Lead 10 also includes two conductive connections in the form of individually isolated coiled wires, each of the two connections preferably being, for example, a respective pair of conductors 12, 12 and 14, 14. These conductive connections run along the entire length of the lead and are connected at the proximal end of the lead to a coupling connector to a generator implant (not shown). Lead 10 also carries a ring electrode 16 connected to a chip 18 providing the multiplexing/demultiplexing functions (as well as to other electrodes located in other parts of the lead) with conductive connections 12, 14 acting as a connection bus between the various electrodes of lead 10 and a remote generator (not shown).

Chip 18 is electrically connected, on the one hand, to electrode 16 and, the other hand, to each of conductive connections 12 and 14.

For convenience and simplicity of the description of a preferred embodiment of the present invention, chip 18 is described here as a multiplexer/demultiplexor of electrode(s), but a person of ordinary skill in the art would understand that the present invention is not limited to this exemplary type of circuit and that chip 18 also or in the alternative may be coupled to a sensor (e.g., a signal transducer that produces an electrical signal representative of the changes of a physical parameter being monitored by the sensor). In this regard, in one embodiment chip 18 may incorporate such a sensor, or include an active electronic circuit such as an amplifier, or filter, with or without a sensor placed nearby, or a micro-electromechanical (MEMS) device, or generally, any active element that may be technologically integrated into a lead body. As contrasted with the structure and electrical interconnections, the multiplexing/demultiplexing, switching, and any signal processing functions of chip 18 form no part of the present inventions.

Chip 18 in this embodiment has two outputs corresponding to conductive connections 12 and 14 of the wire bus, and a third output for connection to electrode 16, and possibly additional outputs in the case, for example, of a multi-electrode configuration (as in the case of FIGS. 9 to 11 described below, comprising a plurality of sector electrodes multiplexed by a single chip).

Figure 1:
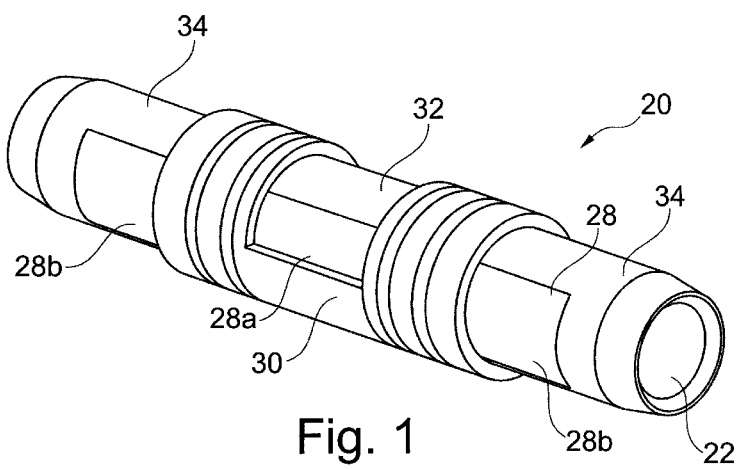
FIGS. 1-8 show the successive steps for manufacturing the section of a first embodiment of the lead including the chip and at least one electrode, with its various components, according to the present invention, with FIG. 1 illustrating a supporting tube before receiving a flexible chip, FIG. 2 illustrating a partial cut-away view of the supporting tube of FIG. 1, FIG. 3 illustrating a partial cutaway view of the supporting tube of FIG. 2 after installation of a flexible chip, FIG. 4 illustrating the supporting tube of FIG. 3 after installation of a conductive sleeve, FIG. 5 illustrating the supporting tube of FIG. 4 after sealing the assembly against the external environment, FIGS. 6 and 7 illustrating the supporting tube of FIG. 5 after being welded to the conductive connection, and FIG. 8 showing a cut-away view of the relevant portion of the lead in its finished state.
Figure 3:
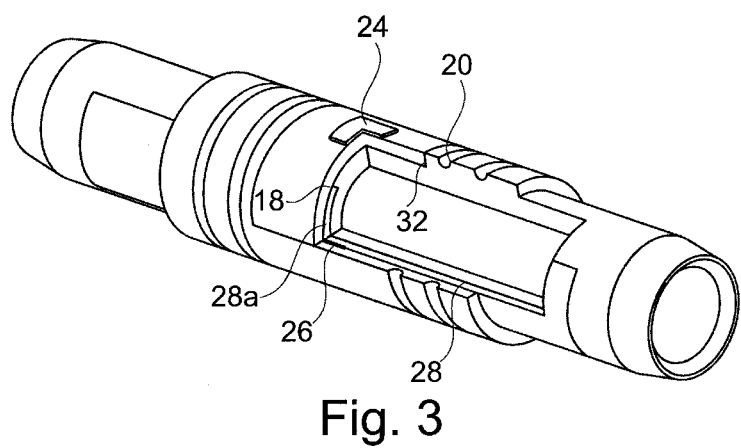

Preferably, chip 18 is mounted on a rigid cylindrical supporting tube 20 made of an insulating material and having a central crossing bore 22 ensuring, with no reduction in diameter, the continuity of the inner lumen of the lead, necessary, for example, for the passage of a stylet or a grommet during an implantation procedure (see FIGS. 1 and 3).

To allow mounting on the cylindrical supporting tube, chip 18 preferably has a flexible substrate, meaning that the substrate is thin enough to be bent and to fit to the cylindrical surface of the substrate. This technique is, for example, described by Zimmermann et al., *A Seamless Ultra-Thin Chip Fabrication and Assembly Process*, Electron Devices Meeting IEDM '06, 11-13 Dec. 2006, pp. 1-3, to which one skilled in the art is referred and which disclosure is hereby incorporated herein by reference. To make chip 18 flexible, it is necessary to thin the substrate (usually a silicon substrate) to a thickness of less than 0.1 mm, so that it can match the shape of tube 20, whose outside diameter is, in the illustrated example, 0.85 mm, where chip 18 is located.

With particular reference to FIG. 3, chip 18 has on an outer (convex) surface on which is located an outer conductive pad 24. Pad 24 is intended to come into contact with electrode 16 (see FIG. 8), and it carries at its opposite (concave) outer surface two internal diametrically opposed conductive pads 26 (only one of pads 26 is visible in the FIGS. 3, 4, and 6-8), intended to be connected, as described below, respectively to conductive connections 12 and 14. These various conductive pads comprise, for example, an alloy of gold that can be soldered by reflow at 450° C. to establish the electrical connections required with the elements just mentioned.

Figure 2:
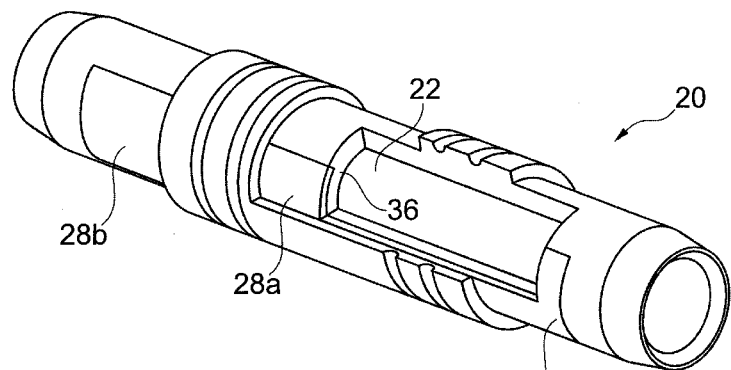

FIGS. 1 and 2 show, separately, supporting tube 20 before it receives flexible chip 18 (FIG. 2 is a cutaway view of FIG. 1 showing in section the internal structure of the tube). Tube 20 is a tube made of an electrically insulating material, preferably constructed by overmolding plastic or ceramic components assembled together by high temperature reflow or by gluing. It has two elongated conductive strips 28, preferably diametrically opposed (one of these strips is visible in the figures) formed on the surface and extending in an axial direction along most of the length of tube 20 to form a crossing, with an apparent central region 28a and two end regions 28b.

Supporting tube 20 comprises a central region 30 of a greater diameter, e.g., 1 mm in the example shown, provided in its surface with a cavity 32 forming a receptacle for flexible chip 18. The depth of cavity 32 substantially corresponds to the thickness of chip 18 so that once chip 18 is established in cavity 32, it is essentially flush with the contour of cavity 32 (as shown in FIG. 3). The configuration of tube 20 is such that central part 28a of crossing strip 28 is visible, i.e., exposed, at the bottom of cavity 32.

Supporting tube 20 also has two end regions 34 of a smaller diameter, e.g., 0.85 mm in the example shown, with two respective ends 28b of crossing conductive strip 28. The length of tube 20 is, in this example, about 5 mm and the surface area of cavity 32 is about 1 to 2 mm$^2$ It should be understood that central bore 22 is completely electrically isolated from crossing strips 28 and from cavity 32, with a wall thickness 36 (as shown in FIG. 2) of supporting tube 20 of about 0.55 mm. This structure helps maintain the electrical isolation while maintaining a relatively large bore diameter.

FIG. 3 illustrates the supporting tube after installation of chip 18 in cavity 32.

Figure 4:
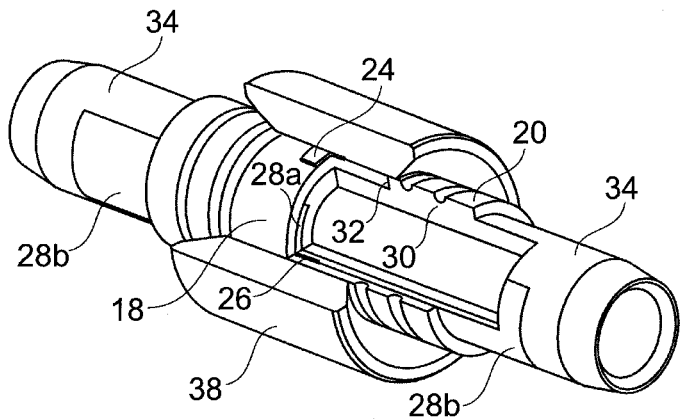

The next step in the manufacturing process, illustrated in FIG. 4, is to put on the assembly a previously obtained sleeve 38 made of a conductive material, fitted to central region 30 of supporting tube 20 and based on the full extent in the axial direction of cavity 32, so that sleeve 38 covers the entire surface of chip 18. A thermal reflow step establishes an electrical connection between each of internal conductive pads 26 of chip 18 and central part 28a of crossing conductive strip 28, thus ensuring electrical continuity between each of these pads and both ends 28b at ends 34 of supporting tube 20. This heating also allows establishing electrical contact between external pad 24 of chip 18 and the conductive material of sleeve 38, for constituting ring electrode 16.

Figure 5:
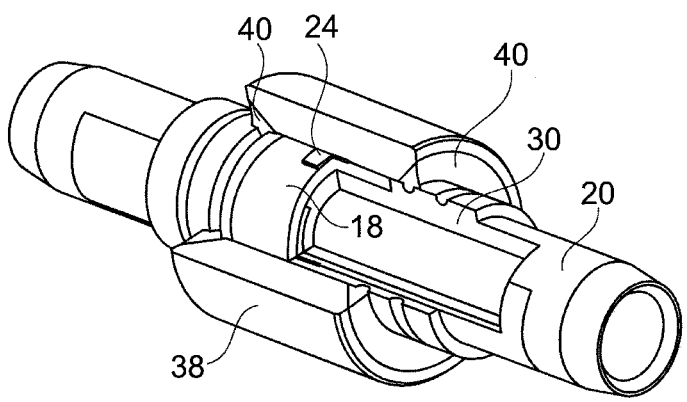

The next step, illustrated in FIG. 5, is to complete the sealing of the assembly with respect to the external environment, by injecting a mass of material 40, such as polyurethane glue, in the space between sleeve 38 and central region 30 of supporting tube 20. In addition to sealing, the mass of glue protects the assembly, including chip 18, in respect of all the constraints and external mechanical stresses, thus ensuring a sustainable and protective encapsulation of the assembly of electrical and electronic components, including during the assembly of lead 10 at the factory.

At this stage, the resulting assembly is ready for a visual inspection and an electrical test of chip 18 functionalities, prior to assembly of the lead body that will now be described.

The next step, shown in FIG. 6, is to establish electrical connections formed by spiral conductors 12, 12 and 14, 14 and to weld these conductors to corresponding pads 28b, for example by a weld 42, 42 between the stripped end of conductors 12, 12 and end pad 28b at the proximal side of the crossing conductive strip located there. Welding is preferably performed by laser welding, and forms no part of the present invention. The same welding step is performed in the diametrically opposite region (not shown in the figure) between conductors 14, 14 of the other electrical connection and the other crossing conductive strip diametrically opposed to that illustrated in FIG. 6.

The next step, illustrated in FIG. 7, is to do the same on the opposite side of annular sleeve 38, i.e., on the distal side, for example by a laser formed weld 44, 44 joining conductors 12, 12 on end 28b at the distal side of crossing conductive strip 28 (and similarly for conductors 14, 14 in the diametrically opposed region).

Once welds 42, 42, and 44, 44 are made, the electrical continuity of conductive connections 12, 12 and 14, 14 is provided on both sides of sleeve 38. Furthermore, a connection is established, as explained with reference to FIG. 4, with each of these connections and the corresponding interior pad of chip 18, for example, as illustrated, between connection 12, 12 and interior pad 26.

The final step, illustrated in FIG. 8, is to coat or cover spiral conductors 12, 12 and 14, 14 on either side of sleeve 38 with a cylindrical isolated sheath 46, for example, made of polyurethane or silicone, having an essentially constant diameter identical to that of sleeve 38. This provides a monodiameter lead, having a typical outer diameter of 1.6 mm (4.8 French), and provided with an internal lumen 22 of at least 0.55 mm (also the diameter of the central crossing bore of supporting tube 20), similar to conventional leads, such as a Xfine TX26D lead manufactured by Sorin CRM, Clamart, France.

By providing one or more supporting tubes 20 interposed between conductor sleeves 38 as successive annular electrodes, it is possible to manufacture a lead comprising at different locations along its length a plurality of electrodes, all multiplexed through a respective corresponding chip disposed underneath the electrode.

Figure 9:
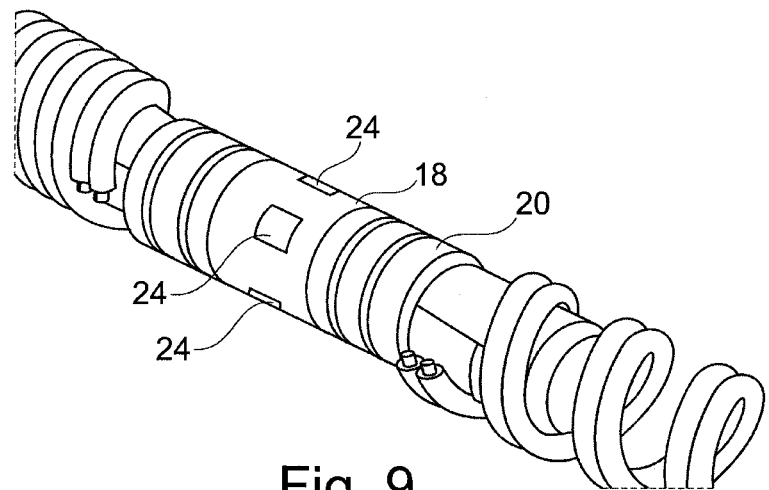
Figure 10:
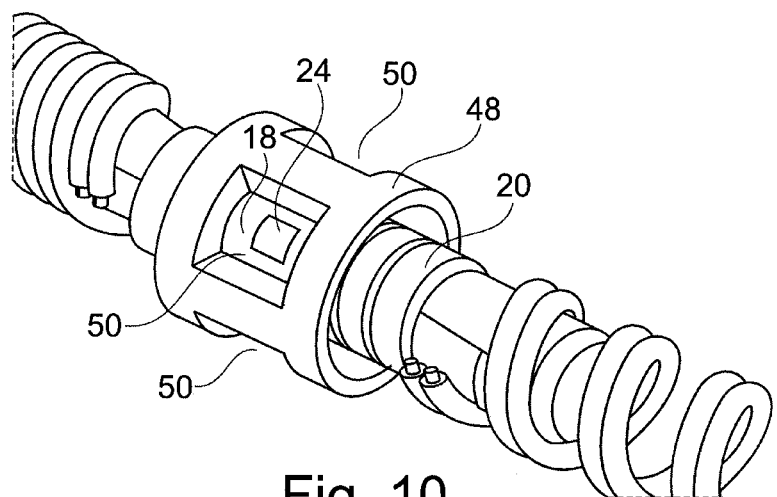
Figure 11:
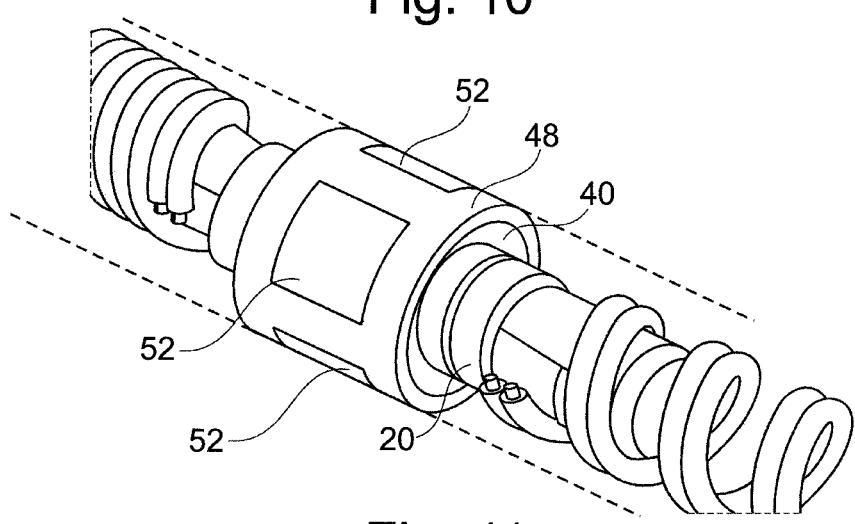

With reference to FIGS. 9-11, a second embodiment of the present invention is illustrated in which conductive sleeve 38 forming annular electrode 16 of the first embodiment described above is replaced by an insulating sleeve 48 of the same diameter, but provided with a plurality of cavities 50, for example, four axially oriented cavities 50, each revealing a conductive pad 24 outside of chip 18. This is realized, instead of a single ring electrode, by a plurality of sector electrodes, for example, oriented in four quadrants, these electrodes being selectable at will by a multiplexing system integrated into chip 18. The latter is provided with a plurality of external conductive pads 24, preferably equal in number to the plurality of sector electrodes, these pads being still visible in the bottom of cavities 50 of sleeve 48 after insertion of sleeve 48 on supporting tube 20 (see FIG. 10).

Sector electrodes 52 are preferably formed by clipping a conductor micromechanical component coming into contact with outer conductive pad 24 of chip 18 and the outer surface of which (which is flush with cylindrical sleeve 48) is the sector electrode itself.

It will be understood by a person of ordinary skill in the art that it is relatively easy to adjust the surface and shape of each sector electrode 50, simply by defining as desired the size and shape of the cavities 50 of insulating sleeve 48.

One skilled in the art will understand the present invention is not limited by, and may be practice by other than the foregoing embodiments described, which are presented for purposes of illustration and not of limitation.

What is claimed is:

1. A lead for an active implantable medical device, comprising:
    an elongated flexible sheath having a central lumen and at least one conductive connection housed in the central lumen of the sheath;
    wherein the elongated flexible sheath and the at least one conductive connection are separated into two or more segments by at least one rigid supporting tube interposed in the sheath, the two or more segments comprising a first segment and a second segment, the supporting tube comprising:
        a central region and two end regions, wherein the central region has a diameter that is greater than a diameter of the two end regions;
        wherein the central region further comprises a cavity, the cavity forming a chip receptacle;
        a chip held in the chip receptacle comprising a substrate and further comprising a first conductive contact pad and a second conductive contact pad;
        an electrode positioned on the supporting tube such that the first conductive contact pad of the chip is connected to the electrode; and
        a conductive strip formed on an outer surface of the supporting tube and extending in an axial direction along a length of the supporting tube, wherein the conductive strip comprises a central portion and two end portions, wherein the second conductive contact pad on the chip is connected to the conductive strip, and wherein a first of the two end portions of the conductive strip is electrically coupled to the first segment of the at least one conductive connection and a second of the two end portions of the conductive strip is electrically coupled to the second segment of the at least one conductive connection.

2. The lead of claim 1, wherein the electrode includes a conductive sleeve circumferentially extending around a periphery of the central region of the supporting tube.

3. The lead of claim 1, wherein the first conductive contact pad is positioned on an exterior surface of the substrate of the chip and the second conductive contact pad is positioned on an interior surface of the substrate of the chip.

4. The lead of claim 3, wherein the chip has a thickness that corresponds with a depth of the cavity such that the exterior surface of the chip is flush with the diameter of the central region of the supporting tube.

5. The lead of claim 3, wherein the substrate of the chip is flexible such that the interior surface of the chip forms to the outer surface of the supporting tube when the chip is held in the chip receptacle.

6. The lead of claim 1, wherein the supporting tube comprises at least one of a ceramic material and a plastic material that electrically isolates the supporting tube.

7. The lead of claim 1, wherein the conductive strip is a first conductive strip, the lead further comprising a second conductive strip, wherein the first conductive strip and the second conductive strip are disposed on diametrically opposed regions of the supporting tube.

8. The lead of claim 1, further comprising an insulating sleeve that defines a plurality of cavities and circumferentially extends around a periphery of the central region of the supporting tube, wherein the electrode comprises a plurality of sector electrodes, one of each of the plurality of sector electrodes disposed with each of the plurality of cavities, wherein the first conductive contact pad comprises a plurality of first conductive contact pads, and wherein each of the plurality of sector electrodes is connected to a corresponding one of the plurality of first conductive contact pads of the chip.

9. The lead of claim 1, wherein the cavity is formed on an outer surface of the central region of the supporting tube.

10. A supporting tube of a lead for an active implantable medical device, comprising:
- a conductive strip disposed on an outer surface of the supporting tube and extending in an axial direction along a length of the supporting tube and including a central portion and two end portions, wherein a first of the two end portions of the conductive strip is configured to be electrically coupled to a first segment of an at least one conductive connection and a second of the two end portions is configured to be electrically coupled to a second segment of the at least one conductive connection; and
- a central region and two end regions, the central region extending from the outer surface of the supporting tube such that the central region has a diameter greater than the two end regions and defining a cavity, the cavity forming a chip receptacle structured to hold a chip; wherein the chip includes an interior contact pad and an exterior contact pad, the conductive strip configured to contact the interior contact pad of the chip.

11. The supporting tube of claim 10, further comprising a conductive sleeve configured as an electrode and circumferentially extending around a periphery of the central region of the supporting tube.

12. The supporting tube of claim 11, wherein the conductive sleeve is structured to contact the exterior contact pad of the chip when the chip is held in the receptacle.

13. The supporting tube of claim 10, further comprising an insulating sleeve defining a plurality of cavities and circumferentially extending around a periphery of the central region of the supporting tube.

14. The supporting tube of claim 13, wherein the supporting tube is configured to couple with a chip having a plurality of exterior contact pads, and wherein each of the plurality of cavities of the insulating sleeve is configured to correspond with one of the plurality of exterior contact pads when the chip is held in the receptacle.

15. The supporting tube of claim 14, further comprising a plurality of electrodes, wherein one of the plurality of electrodes is disposed within each of the plurality of cavities such that each of the plurality of electrodes is contacting one of the plurality of exterior contact pads of the chip when the chip is held in the receptacle.

16. The supporting tube of claim 10, wherein the cavity has a depth configured to correspond to a thickness of the chip, such that the diameter of the central region of the supporting tube is flush with an exterior surface of the chip when the chip is held in the receptacle.

17. The supporting tube of claim 10, wherein the supporting tube is shaped such that an interior surface of the supporting tube forms to the interior surface of the chip when the chip is held in the chip receptacle.

18. The supporting tube of claim 10, wherein the conductive strip is a first conductive strip, the lead further comprising a second conductive strip, wherein the first conductive strip and the second conductive strip are disposed on diametrically opposed regions of the supporting tube.

19. The supporting tube of claim 18, wherein the supporting tube is configured to couple with a chip having a first interior contact pad and a second interior contact pad, and wherein the first conductive strip is configured to contact the first interior contact pad and the second conductive strip is configured to contact the second interior contact pad when the chip is held in the receptacle.

20. The supporting tube of claim 10, wherein the cavity is formed on an outer surface of the central region of the supporting tube.

* * * * *